United States Patent
Whitney et al.

(10) Patent No.: US 7,230,233 B2
(45) Date of Patent: Jun. 12, 2007

(54) ANALYSIS OF DATA FROM A MASS SPECTROMETER

(75) Inventors: Jeffrey L. Whitney, Robbinsville, NJ (US); David J. Detlefsen, New Hope, PA (US); Mark E. Hail, Yardley, PA (US)

(73) Assignee: Novatia, LLC, Monmouth Junction, NJ (US)

( * ) Notice: Subject to any disclaimer, the term of this patent is extended or adjusted under 35 U.S.C. 154(b) by 0 days.

(21) Appl. No.: 11/277,134

(22) Filed: Mar. 21, 2006

(65) Prior Publication Data

US 2006/0219894 A1 Oct. 5, 2006

Related U.S. Application Data

(62) Division of application No. 10/856,736, filed on May 28, 2004, now Pat. No. 7,049,581.

(60) Provisional application No. 60/475,227, filed on May 30, 2003.

(51) Int. Cl.
*G06F 19/00* (2006.01)
(52) U.S. Cl. .......................... 250/282; 702/23; 702/27
(58) Field of Classification Search .................... None
See application file for complete search history.

(56) References Cited

U.S. PATENT DOCUMENTS

| 5,538,897 | A | | 7/1996 | Yates |
| 6,017,693 | A | | 1/2000 | Yates |
| 6,085,153 | A | * | 7/2000 | Hirsh et al. .................... 702/23 |
| 6,272,436 | B1 | * | 8/2001 | Hirsh et al. .................... 702/27 |

* cited by examiner

*Primary Examiner*—David Vanore
(74) *Attorney, Agent, or Firm*—William H. Eilberg

(57) ABSTRACT

A programmed computer analyzes data from a mass spectrometer. A spectrum corresponding to an unknown sample is perturbed in various ways, and each perturbed spectrum is compared with the spectrum of a known or reference substance. The perturbed spectrum having the highest correlation with the known spectrum, and which is also physically plausible, is considered to be the best fit. The method indicates in what specific ways the unknown sample differs from, or is similar to, the known substance.

2 Claims, 9 Drawing Sheets

ANALYSIS OF DATA FROM A MASS SPECTROMETER

CROSS-REFERENCE TO PRIOR APPLICATIONS

This is a division of U.S. patent application Ser. No. 10/856,736, filed May 28, 2004 now U.S. Pat. No. 7,049,581, which claims the priority of U.S. Provisional Patent Application Ser. No. 60/475,227, filed May 30, 2003.

BACKGROUND OF THE INVENTION

This invention relates to the field of mass spectrometry, and provides a method and apparatus for analyzing data obtained from a mass spectrometer.

Mass spectrometers have long been used for performing qualitative analysis of substances. A mass spectrometer can essentially reduce a test sample to a set of ionic components, and displays the mass, and relative abundance, of each such component. The mass spectrometer produces an output that can be represented as a graph showing the mass of each component (for example, on the horizontal axis) and the intensity, or relative abundance, of each component (for example, on the vertical axis). The graph generated by a mass spectrometer is called a "spectrum".

Examples of the use of mass spectrometry in the field of biological science are given in U.S. Pat. Nos. 6,017,693 and 5,538,897, the disclosures of which are incorporated by reference herein.

A major problem in the use of a mass spectrometer is in the analysis of the spectrum generated by the device. Typically, an unknown substance is to be evaluated and compared with the spectrum of a known substance. A simple visual comparison of the spectrum of the unknown substance with a known spectrum is often insufficient and unproductive, as the points of similarity between the spectra are often not apparent to the human observer.

Even numerical methods of comparison of spectra, known in the prior art, have been unsatisfactory. It has been known to calculate correlations between spectra, but such calculations have been cumbersome and impractical.

The present invention provides a computer-based method of analyzing spectra from a mass spectrometer. The method of the present invention enables the user to obtain information about the spectrum of a test sample, even where such information is not intuitively obvious or readily observable.

SUMMARY OF THE INVENTION

The present invention derives inferences concerning the composition of an unknown sample, by comparing each of a set of perturbed spectra with a spectrum corresponding to a reference substance. The spectrum of the unknown sample is perturbed, in various ways, by introducing a shift of one or more ionic components in the spectrum. The shifts introduced may be derived by "brute force", such as by using all available integers or decimals, or they may be chosen according to experimental data describing known shifts caused by the presence of certain substances. Each of the perturbed spectra are then cross-correlated with the reference spectrum, and the perturbed spectrum having the highest correlation, and representing a physically plausible or application-relevant result, is deemed the "best" fit.

The perturbed spectrum that is considered the best fit can be used to draw inferences about how the unknown sample differs from, or how it is similar to, known or reference compounds. In particular, the method of the invention makes it relatively easy to infer the presence of specific ions in the unknown sample, based on the above-mentioned differences from, or similarities to, known or reference samples.

The above-described method is preferably performed by a programmed computer that automates the correlation function. The invention therefore includes the method of performing the data analysis, and well as the programmed computer, or equivalent device, that is used to perform the method.

The invention therefore has the primary object of providing an automated method for analyzing data from a mass spectrometer.

The invention has the further object of providing a method and apparatus for determining the specific ways in which an unknown substance differs from, and/or is related to, a known or reference substance.

The invention has the further object of providing a method of qualitative analysis, which method uses experimental data concerning the effect of the presence of specific substances, to draw inferences about the composition of a material.

The invention has the further object of reducing the computation time required in the above-described method, by providing a technique for discarding ions and/or shifts that are not likely to yield useful results.

The reader skilled in the art will recognize other objects and advantages of the present invention, from a reading of the following brief description of the drawings, the detailed description of the invention, and the appended claims.

DETAILED DESCRIPTION OF THE INVENTION

Figure 1:
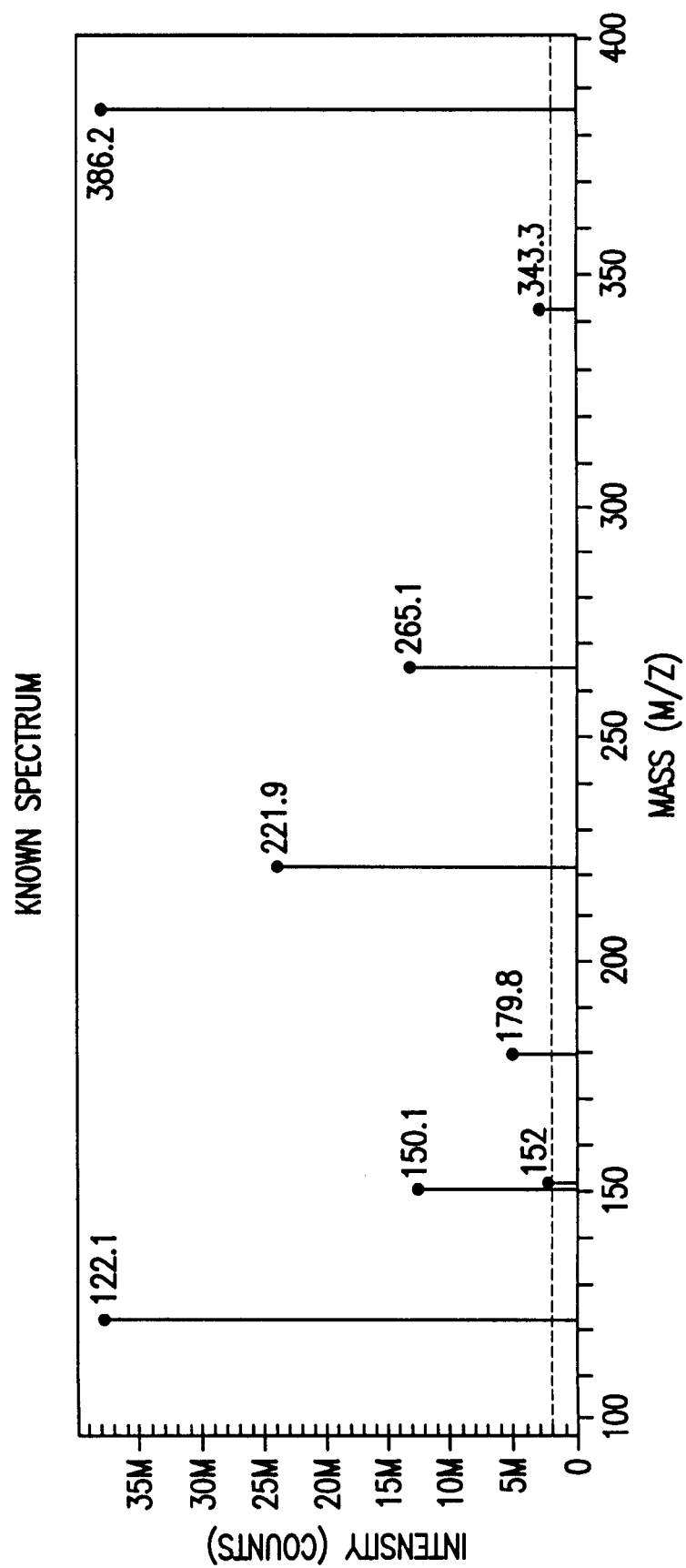
FIG. 1 provides a graph representing the spectrum of a known substance, in a hypothetical example of the use of the present invention.

The present invention includes a method of processing data, obtained from a mass spectrometer, to draw inferences about the composition of a sample material. The invention is especially useful in analyzing metabolites, impurities, and degradants that result from a given chemical substance, such as a pharmaceutical, but is not limited to use in the latter fields. The general method will first be described in the following overview, after which more specific details and examples will be given.

Overview

A mass spectrometer separates various charged components in a substance according to their mass to charge ratio. The mass spectrometer produces an output called a spectrum, which is essentially a graph whose data points correspond to ionized components in the sample. Analysis of the spectrum provides information about the molecular structure of the sample.

In this specification, the term "ion" is used in its broadest sense, to include any charged particle that can be detected by the mass spectrometer. The term "ion" is sometimes also used to refer to a point or vertical bar on a spectrum produced by a mass spectrometer, because the mass spectrometer separates and counts charged particles, and each point or bar on the spectrum corresponds to a charged particle detected by the instrument.

Each spectrum obtained from a mass spectrometer typically comprises a graph whose horizontal axis represents the masses of given ionic components of a sample being tested, and whose vertical axis represents the intensity of those ionic components, usually expressed in terms of the number of "counts" recorded by the mass spectrometer. In brief, the vertical axis indicates the relative abundance of a given component in the sample. Each compound usually has its own unique spectrum, as viewed using certain modes of mass spectrometric analysis, the spectrum containing a particular set of ions, and having a particular set of horizontal distances between ions, as viewed on the graph. Typically, similar ions correspond to the same substructure contained in the compounds being compared, and differences between the ions in the samples indicate structural differences. Compounds related structurally tend to produce spectra that are related, i.e. having similar ions and/or similar differences between ions.

The spectrum produced by the mass spectrometer can be easily reduced to numerical, and hence to digital, form. The spectrum can be stored, for example, as a set of ordered pairs, each ordered pair representing the Cartesian coordinates of a point on the spectrum. More generally, the horizontal axis is typically subdivided into "bins" having a finite width, and the spectrum is stored in terms of the number of "counts" that are found within each bin.

The present invention uses the fact that the presence of certain ions in a sample will cause predictable changes in the appearance of the spectrum. Compounds that differ by one substructure, such as a hydroxyl group, exhibit that difference in the spectra obtained from the mass spectrometer. That is, the spectrum contains one ion which is "shifted" by an amount (measured in molecular mass units) corresponding to that hydroxyl group. More generally, the presence of a particular ion will cause a shift, to the left or to the right, of a given point on the spectrum. This shift is expressed in terms of the mass units used on the horizontal axis. Thus, a sample which contains an ion having a mass of 200 units, when chemically or biologically modified with a known moiety to cause a shift in mass of +16 units, can be expected, under normal circumstances, to exhibit an ion located at a position corresponding to a mass of 216 units.

The present invention is typically used to compare a spectrum of an unknown substance with the spectrum of a known substance. However, the invention can also be used where both spectra relate to unknown substances. That is, the invention can be used to determine how an unknown substance is similar to, or different from, some other unknown substance. Thus, in its broadest sense, the invention compares the spectrum of an unknown substance with the spectrum of a reference substance, and the reference substance may be known or unknown. In this specification, the term "known" will be used to describe the spectrum of the reference substance, but it is understood that this term includes the case where the reference substance is itself unknown. The methodology is exactly the same, whether the reference substance is known or unknown.

In its most basic form, the method of the present invention starts with a spectrum of a known or reference substance, and a spectrum of the substance being analyzed. These spectra are stored in numerical form for ease of manipulation. The method comprises repeatedly perturbing the spectrum of the unknown substance, by known shifts, to obtain a set of distinct, perturbed spectra, and correlating each such perturbed spectrum with the known spectrum. That is, one compares a large number of different spectra, each one being obtained by perturbing the spectrum of the unknown substance, and numerically comparing each of such spectra with the spectrum of the known substance. The spectrum having the greatest correlation, while still being physically plausible and application-relevant, is deemed the best fit. The result is that one can characterize the unknown spectrum in terms of a known spectrum that is shifted by the presence of one or more ions.

In this specification, the terms "shift" and "perturbation" are used interchangeably.

The perturbations imposed on the spectrum of the unknown substance can be derived in at least the following two ways. First, the user may start with a list of known perturbations, corresponding to a set of known or expected chemical modifications. The shifts caused by various chemical modifications, in the spectra produced by a mass spectrometer, can be predicted from experimental observation, and these shifts are commonly known and available to the researcher. In using the list of known perturbations, the method can be practiced by trying any or all of these perturbations, to find a modified or perturbed spectrum that most closely correlates with the known spectrum. Secondly, the perturbations applied to the spectrum of the unknown substance may be unrelated to experimental data. For example, one can perturb the points on the spectrum by every possible positive and negative value, up to a predetermined limit. The methodology is the same as before, except that the perturbed spectrum having the highest correlation to the given spectrum may not correspond to a real substance. That is, by imposing arbitrary perturbations, the results obtained may not always be physically meaningful, and additional analysis may be necessary to insure a reasonable result.

EXAMPLE

This is a simplified example that shows the operation of the present invention. Suppose that an unknown spectrum contains two ions, having mass values of 100 and 200, respectively. Suppose further that the user selects two perturbations, or shifts, having the values +10 and −20, respectively. Then every possible combination of ions and shifts are as shown in Table 1, below. Each entry in the table represents a perturbed spectrum, and each such perturbed spectrum will be compared, numerically, with the known spectrum.

TABLE 1

1) 100, 200
2) 100 + 10, 200
3) 100, 200 + 10
4) 100 + 10, 200 + 10
5) 100 − 20, 200
6) 100, 200 − 20
7) 100 − 20, 200 − 20
8) 100 + 10, 200 − 20
9) 100 − 20, 200 + 10

The comparison of each perturbed spectrum, with the known spectrum, can be done by any known numerical method. A preferred method is to compute a correlation coefficient between the spectra being compared. The case of perfect correlation is defined as the correlation between a spectrum and itself. The degrees of correlation can be represented on an arbitrary scale, such as a range of 0–1, or 0–100, or some other range, the results of the correlation analysis being normalized to fall within the desired range, as is well known in the art. The present invention is not limited to any specific method of performing the comparison.

The result is a list of correlation coefficients, each representing the result of the comparison between one of the perturbed spectra and the known spectrum.

This list of correlation coefficients can be used to "score" the perturbed spectra. Usually, the perturbed spectrum having the highest score, i.e. having the highest correlation to the known spectrum, is the one that is chosen. However, application logic is included in the program, which logic is taken into account when the perturbed spectra are scored, such that the "best" perturbed spectrum is not necessarily the one with the highest correlation coefficient.

As a result of the present method, one can characterize the unknown spectrum in terms of the known or reference spectrum, with the addition or removal of one or more shifts.

Figure 2:
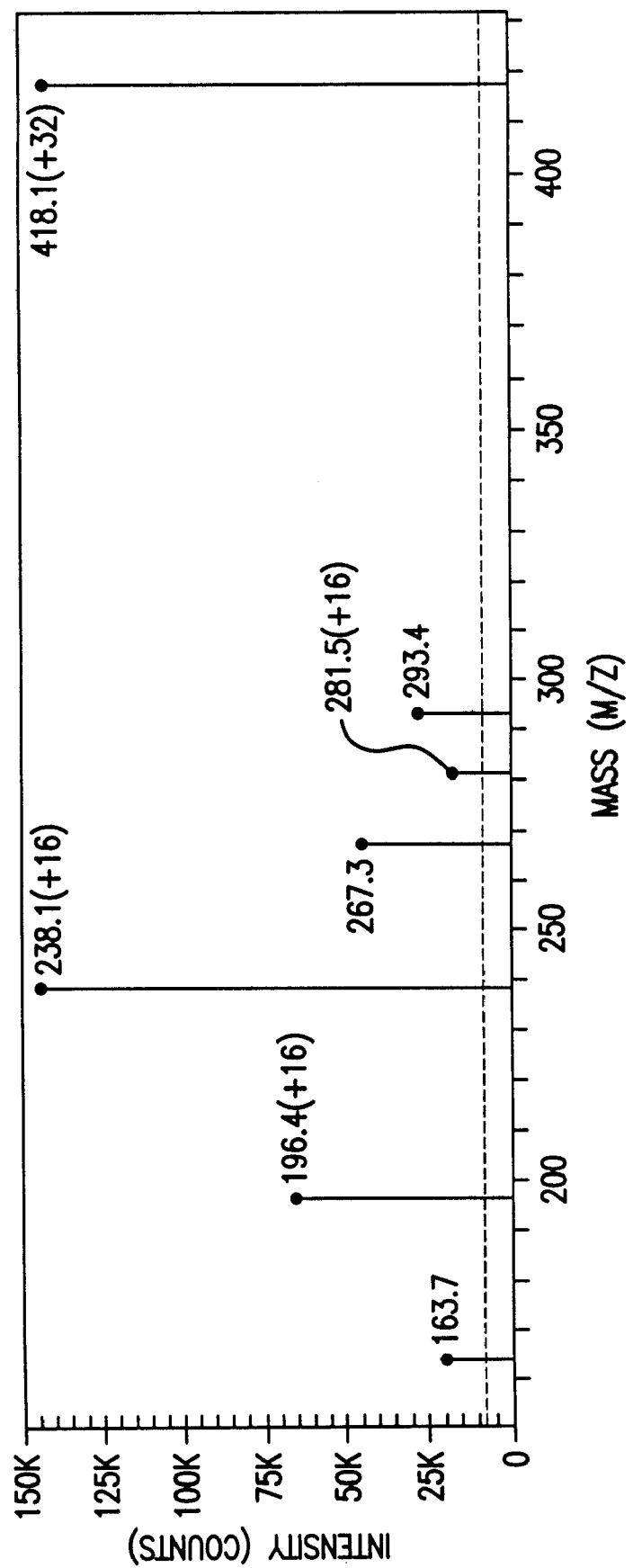
FIG. 2 provides a graph representing the spectrum of a hypothetical unknown substance, in an example of the operation of the present invention, the graph indicating perturbations that make the spectrum correlate most closely with the spectrum of the known substance.

FIG. 1 provides an example of a hypothetical known spectrum. FIG. 2 provides an example of a hypothetical spectrum of an unknown substance, indicating shifts to be applied to each data point. FIG. 2 illustrates the choice of a "best" result, i.e. the perturbed spectrum of the unknown substance which has a high correlation with the known or reference spectrum, and which is application-relevant. These figures are explained in more detail below.

Practical Details

The Choice of Perturbations

As explained above, the shifts or perturbations to be applied to the spectrum being analyzed can be taken from experimental data, or they can be selected mechanically, using a "brute force" method wherein an exhaustive set of possible perturbations are all considered. Table 2 shows various chemical modifications, and the shifts known to be caused by the presence of such chemical modifications, expressed in the same units as shown in the drawings.

TABLE 2

| | |
|---|---|
| −56 | Di-deethyl |
| −32 | Decarboxylation |
| −30 | Deoxy/Demethyl |
| −28 | De-ethylation [O, N, S] |
| −18 | Des-fluoro |
| −14 | Des-methyl |
| −14 | Demethylation [O, N, S] |
| −9 | Des-Chloro/+CN |
| −9 | CN->OH |
| −2 | Dehydrogenation |
| −1 | Oxidative deamination |
| +2 | Des-methyl/Hydroxylation |
| +5 | CN->CH$_2$OH |
| +7 | Hydroxylation/CN->OH |
| +14 | Ketone |
| +14 | Methylation |
| +16 | N-oxide |
| +16 | Sulfoxide |
| +16 | N-oxide |
| +16 | Hydroxylation |
| +16 | Epoxidation |
| +30 | Hydroxy/Ketone |

TABLE 2-continued

| | |
|---|---|
| +30 | Methoxy |
| +32 | Dihydroxylation |
| +34 | Dihydro diol |
| +42 | Acetylation |
| +44 | Des-Chloro/Bromination |
| +80 | Sulphate |
| +96 | Hydroxy/Sulphate |
| +161 | N-acetyl Cysteine |
| +176 | Glucuronide |
| +192 | Hydroxy/Glucuronide |
| +305 | Glutathione |

Any or all of the perturbations shown in Table 2, or other perturbations corresponding to other chemical modifications, may be used. The computer which operates the method preferably includes a memory in which these perturbations are stored, so that the computer can apply them as described above. The computer may be programmed to allow the user to select certain perturbations, or to apply automatically all possible combinations of perturbations, as illustrated in the Example, without guidance from the user.

It should be appreciated that the preferred method of perturbing the spectrum of the unknown substance is to subtract the known shift caused by a particular chemical modification. For example, if one wants to evaluate whether a particular substance has been hydroxylated, one perturbs the ions produced from that substance by "removing" the hydroxyl, i.e. by subtracting 16 units from the position of the pertinent ion, because the table shows that the effect of hydroxylation is to shift the ion by +16. Similarly, for chemical modifications that cause negative shifts, removal of those modifications is simulated by adding the absolute value of the pertinent values shown in the table.

Note that the decision whether to add or subtract a perturbation is important to the extent that it helps the user to obtain meaningful results. However, the computational methodology of the present invention is unaffected by whether perturbations are added or subtracted. If perturbations are applied without regard to their physical meaning, the results may not always be usable.

In an extreme case, the computer could simply apply perturbations comprising, for example, all values between, say, −500 and +500, and generate spectra having all possible combinations of such perturbations. The perturbations could be integral or non-integral. The major limit on the number of such possible perturbations is dictated by the computing resources available and the computation time required.

MS/MS Mode versus Normal Mode

In the description given above, no consideration was given to the various possible modes of operation of the mass spectrometer. In general, a mass spectrometer can operate in "normal" mode, which means that it simply provides a spectrum showing the relative concentration of all ionizable components in the sample.

In many applications, only one ion is of interest. But if one limits the inquiry to ions having only one particular mass, the spectrum produced will have only one data point, and the number of available perturbations is small. It is therefore often convenient to use the "MS/MS" or "MS$^n$" mode, wherein the spectrum includes not only information about the basic ion being studied, but also information about ions produced by collision-induced dissociation.

In brief, the ion being studied can be caused to collide with gas molecules, causing the ion to dissociate into substructural fragment ions. These fragments are themselves smaller ions which can be analyzed by the mass spectrometer. The signature of a particular compound therefore includes not only the ion of interest, but other ions that are produced in collisions with gas molecules. When in MS/MS or MS$^n$ mode, the mass spectrometer displays information concerning the original ion, as well as the collision-dissociated products. The collision products are represented as points on a spectrum, and each can be perturbed in the manner described above, to infer information about the structure of the substance being studied. Display of the collision products therefore represents a substance using a finer structure, making it possible to obtain more detailed information about the substance.

It should, however, be appreciated that the method of perturbing the points on the spectrum, and comparing each perturbed spectrum with a known spectrum, is the same, in principle, regardless of whether the mass spectrometer is operating in normal mode or in MS/MS mode.

Operation of the Method

In operating the method of the present invention, it is desirable first to pre-process the data of each spectrum, so that the data are normalized and in a suitable format for mathematical manipulation. Details of the pre-processing are given below. Also, it is helpful to rank the importance of each ion in the unknown spectrum, and the importance of each shift to be applied. If such a ranking can be accomplished, the system can avoid the need to test ions and shifts which will not contribute to overall correlation increases with the known or reference spectrum, as well as meaningless combinations of ions and shifts. As is apparent from the example given above, the amount of computation time increases exponentially as the number of ions and shifts increases, and even if a supercomputer is available, it may be necessary to take steps to limit the number of computations required.

A preferred method of ranking the ions and shifts is as follows. Each ion in the unknown spectrum which is not present in the known or reference spectrum, i.e. each ion which is unique to the unknown spectrum, and which is above a minimum relative intensity threshold that is user-defined, is separately perturbed using all shifts defined in the program. This process is performed in the same manner as the perturbation approach described above, but using only a single ion at one time, and using all possible shifts. The result is a set of all possible spectra containing the current unknown ion, as modified by all possible shifts. In other words, one obtains a set of modified unknown spectra based on a single ion, and representing all possible shifts applied to that ion.

Each modified unknown spectrum in the above set is compared to the known or reference spectrum using cross-correlation or any other method of numerical comparison. The highest correlation from each ion perturbation set is selected, whereby that correlation result represents that ion relative to all other ions processed in the same manner. The individual ion scores are ordered, highest to lowest, in terms of the correlation values obtained. Ions having a score below a user-defined minimum are removed from further consideration. The highest n ions, in terms of correlation, are selected, where n is determined by a user-defined maximum number of ions to be allowed.

The result is a subset of all possible unknown ions whose rank and total number meet the above-described ranking criteria. Only these ions are considered for further processing.

A similar process is used to rank each shift. Each shift is evaluated individually. For a given shift, all ions above a user-defined threshold are perturbed by that shift, in all possible combinations. A set of all modified unknown spectra, after applying the above combinations, is produced and compared to the known or reference spectrum, as described above. Only the shifts chosen using the above approach are considered for further processing.

In short, the ranking method is similar to the basic method of analysis, except that only one ion, or only one shift, is considered at a time. By discarding the ions or shifts that are unlikely to produce high correlations, considerable computing time can be avoided.

The following provides details about the pre-processing of data. A mass spectrometer, operating in centroid mode, typically returns mass/intensity data pairs which refer to a set of ionic components, as described above. The term "profile mode" refers to acquisition of continuum mass spectral data that are acquired at a constant sampling interval or resolution. Typically, each detected ion in profile mode resembles a Gaussian shaped peak. Centroid mode includes converting each profile peak to a weighted average determination of peak center. A centroided mass is typically represented by a vertical bar having a theoretically zero thickness, representing an exact reading of mass.

The mass portion of each data pair is usually a floating-point value having integer and decimal parts. The decimal part is typically calculated with a precision of four or more significant figures. The intensity portion is usually an integer. Since the precision of the mass portion reported by the instrument is often higher than the actual accuracy of the instrument, it is often desirable to reduce the precision of the mass values to a level which is just below the typical accuracy of the instrument, or in the case of the present invention, a user-defined degree of precision corresponding to the desired number of significant figures. In this way, any variability between two mass measurements made on the same ionic component at different times, say 123.1234 and 123.3234, is removed, thus giving exactly the same, less-precise mass measurement value for the same ionic components.

The reduction in mass measurement precision is also beneficial for subsequent correlation analysis. Many modes of correlation analysis require the input data to be placed in "bins". The speed of the correlation calculation is often determined by the total number of bins present. Typical correlation analysis is performed "bin-to-bin", meaning that similar values contained in the same corresponding bin position tend to make the correlation coefficient higher. It is therefore important to make sure that the mass spectrometric data for each spectrum is pre-processed, or "binned", in a way that guarantees that common ions between correlated spectra are placed in the same corresponding bin position. For purposes of the present invention, a bin position corresponds to the mass portion of a given ion data pair, and the value placed in the bin corresponds to the intensity portion.

The following steps are performed to convert each mass/intensity pair in a given spectrum, thus producing the pre-processed, or "binned", form of that spectrum:

1. If needed, convert all mass spectra acquired in profile mode to centroid mode. This is standard practice in the field, and is typically done using the software included by the instrument vendor, resulting in a single mass/intensity pair for each ion component observed in a mass spectrum. All examples in this disclosure assume that all mass spectra were acquired in centroid mode or converted thereafter.

2. Reduce the precision of each mass value to some user-defined precision value. This can be done using one of many different approaches. For all examples shown in this disclosure, each mass value was simply truncated to produce the integer form, which corresponds to a precision value of 0. However, more elaborate approaches can be used which take into account theoretical decimal contributions based on chemical composition trends which occur relative to mass. These more elaborate approaches typically have the net effect of providing a decision point either to round up or round down a mass value based on its overall mass, assumed chemical composition, and desired precision value. Also of note, it is desirable for the user of the present invention to apply the same approach to shifts or perturbations that refer to known chemical modifications being considered in the algorithm. This is ultimately left up to the user, since the list of shifts or perturbations is user-defined and fully customizable. For the examples shown in this disclosure, all included shifts or perturbations corresponding to known chemical modifications were determined based on a precision value of 0.

3. Relate each converted mass value to a particular bin position/number. The bin position for any given converted mass value is typically (10^precision value)×(converted mass value). For all examples shown in this disclosure, the converted integer mass value itself determines the bin number, since a precision value of 0 was used. For example, 10^0×123=123. As another example, a precision value of 1 and converted mass value of 123.4 would correspond to a bin position of 1234.

4. Normalize all intensity values in a given spectrum based on a range between 0 and 1. Basically, this step is done by dividing all intensity values in a given mass spectrum by the maximum intensity value in that set.

5. Place the normalized intensity of each mass/intensity data pair in the corresponding bin position, as determined in Step 3, above.

6. For any two pre-processed spectra to be correlated, normalize each spectrum so that they have the same number of bins. This normalization is distinct from the normalization of intensities discussed above. For all examples shown in this disclosure, the number of bins between correlated pre-processed spectra are normalized by zero-filling the spectrum containing fewer bins up to the same number of bins contained in the larger spectrum. For example, if pre-processed spectrum 1 has a total of 400 bins, i.e. the highest normalized intensity corresponds to a bin position of 400, and spectrum 2 has a total of 500 bins, 100 bins containing a value of 0 are added to the end of spectrum 1, thus creating two pre-processed spectra with the same number of total bins.

All references, in this disclosure, to ion, mass, unknown spectrum, or known spectrum, are assumed to refer to the pre-processed forms as described above.

Subject to the above limitations, one supplies to the program a list of known ions, a list of unknown ions, and a list of shifts.

The method as described above is then performed, by producing a set of all possible combinations of selected unknown ions, as modified by any or all of the shifts on the list. The modifications are preferably made by subtracting the shifts, as described above.

In a preferred embodiment, the program includes logic that prevents specific shift combinations from being made, based on mathematical and application considerations.

Finally, the perturbed or modified spectra are correlated with the known spectrum. For each correlation, the system stores the modified ions and the shifts used, and the corresponding correlation coefficient.

After the correlation scores are obtained, it is necessary to choose a "best" perturbed spectrum, i.e. a spectrum being most closely related to the known spectrum. Knowledge of the best spectrum helps to show how the unknown spectrum is similar to, and how it is different from, the known compound, so as ultimately to provide information on molecular structure.

Most of the information derived from the "best" perturbed spectrum comes from how the ions were shifted to produce an enhanced correlation. For example, ion 300 may have been shifted by −16, to place the ion at 284, causing the ion to become aligned with a 284 ion in the known spectrum, causing the correlation coefficient to become very high. This result might indicate, in the field of metabolism, for example, the hydroxylation of substructure 284 of the known compound. Information also comes from ions that were not shifted, especially ions common to both the unknown and the known or reference spectra.

The example given in FIGS. 1 and 2 provides further illustration of the above principles. The "best" perturbed spectrum, shown in FIG. 2, represents the "best" combination of shifted ions, and the figure shows the corresponding shifts in parentheses. If one were to apply the labeled shifts to the corresponding ions (i.e. by removing the shifts), the result is a perturbed unknown spectrum having a high correlation with the known spectrum (FIG. 1), after all possible combinations of ions and shifts have been evaluated. Application logic is also used to remove perturbation results containing combinations that are unlikely for a particular application area. For the unknown spectrum, this "best" combination is:

163.7 (zero shift)
196.4 (+16 shift)
238.1 (+16 shift)
267.3 (zero shift)
281.5 (+16 shift)
293.4 (zero shift)
418.1 (+32 shift)

The above result could be interpreted to indicate that the known compound is being hydroxylated (i.e. a shift of +16) at two different locations, with ions 196, 238, and 281 showing individual hydroxylations and ion 418 showing both.

The above example illustrates the usefulness of the present invention in deriving information about the molecular structure of an unknown substance, based on correlation with a spectrum of a known or reference substance, and possibly based on knowledge of the molecular structure of the known or reference substance.

FIGS. 3–8 illustrate an application of the method described above. The illustrated application involves the use of the procedure known in the art as LC/MS (liquid chromatography/mass spectrometry). In a liquid chromatograph, components are separated by the LC device over a period of time, and introduced into the mass spectrometer for collection of mass spectra at distinct time intervals. The result is a collection or series of mass spectra, taken over a period of time, in normal mode and/or MS/MS mode, corresponding to the separated components from the LC device.

The methodology of the present invention can be used to find, and remove from further consideration, common components appearing in two distinct samples analyzed by LC/MS. In the field of LC/MS, this is often called "background subtraction". The present invention is applied in this manner by correlating MS/MS spectra from the two analyzed samples over time.

For example, LC/MS can be applied to two samples containing common and unique components. Typically, one of the samples, the "known" or "blank" sample, contains components either of known origin or of no interest. The second sample, called the "unknown" or "assayed" sample, may contain the same known components as well as unique components of interest. Often the same LC method is used to separate both samples physically for comparative purposes. Common components will separate in a similar manner over time. Components common to both the known and unknown samples are found by using the methodology of the present invention to correlate unperturbed MS/MS spectra from both samples over time.

In practicing the technique of background subtraction, as applied using the present invention, one first obtains all MS/MS spectra from the known MS chromatogram within a user-defined time window, centered around the current unknown MS/MS time, such that the parent mass (also known in the art as the precursor ion) is the same as the parent mass (or precursor ion) of the unknown MS/MS spectrum. If there are no MS/MS spectra present in the time window of interest, having the same parent mass as in the unknown MS/MS spectrum, the current unknown spectrum is considered distinct from the known spectra, and is considered of sufficient interest to warrant further testing.

In addition to the above criterion, a decision may be made to retain an unknown spectrum, for further analysis, based on the following considerations. A common component is defined by the presence of one or more highly correlated MS/MS spectra present in both samples, in the same user-defined time window. Two spectra are considered highly correlated, for purposes of this invention, by having an unperturbed correlation value which is above some user-defined level. MS/MS spectra in the unknown sample that are not highly correlated with any MS/MS spectra in the known sample, in the same user-defined time window, are considered unique to the unknown sample. Also, a common component can still be considered unique to the unknown sample if the corresponding normal mode or MS/MS mode signal between the known and unknown sample is higher than a user-defined difference level. This process is repeated for each MS/MS spectrum in the unknown sample. Components considered unique to the unknown sample are selected for further consideration, whereby their normal mode and/or MS/MS mode spectra are correlated to the known mass spectrum using the perturbation approach previously described. More precise logic for determining when to select a spectrum for further consideration is given below.

Figure 3:
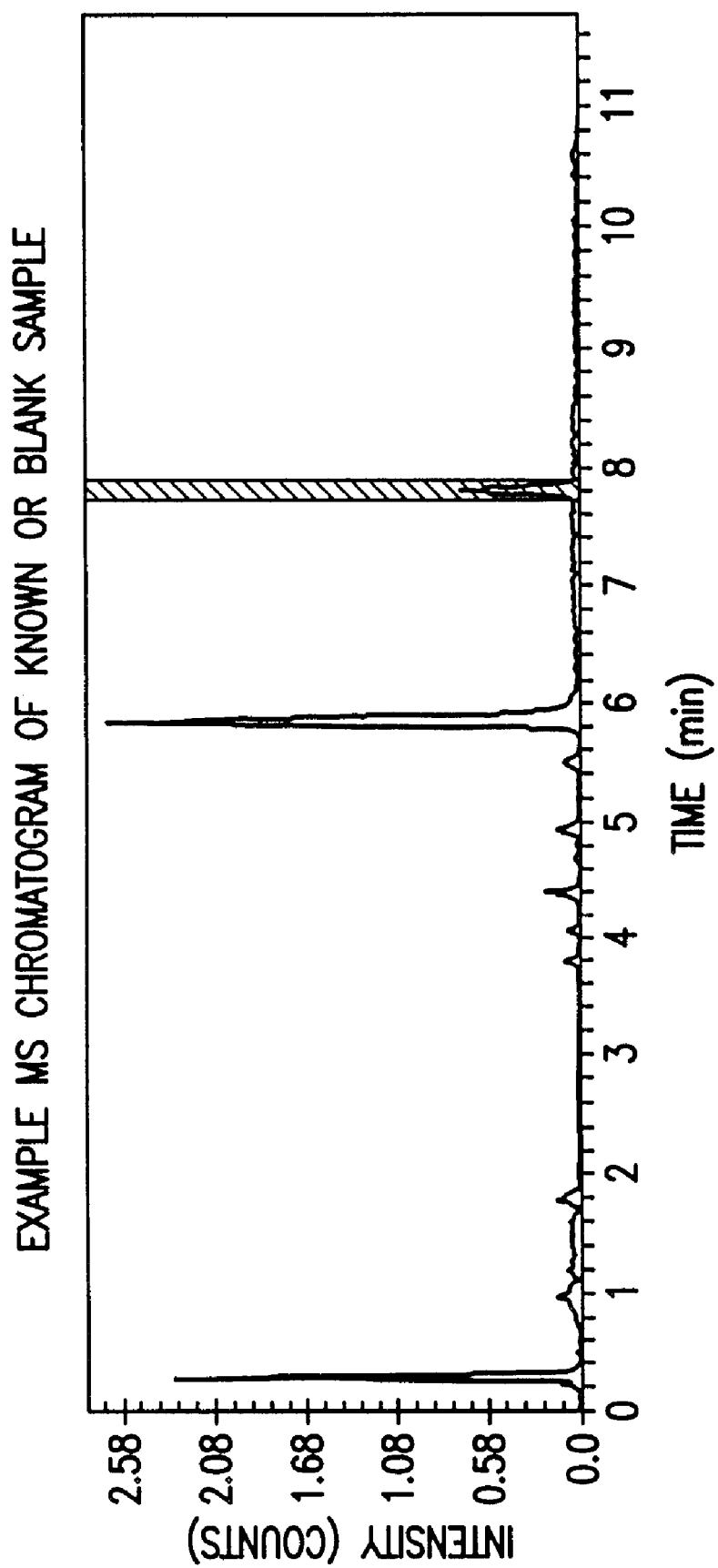
FIGS. 3 and 4 provide graphs which illustrate the application of the present invention to a series of mass spectra taken over a period of time, these graphs showing the total intensity of each spectrum, for each point in time.
Figure 4:
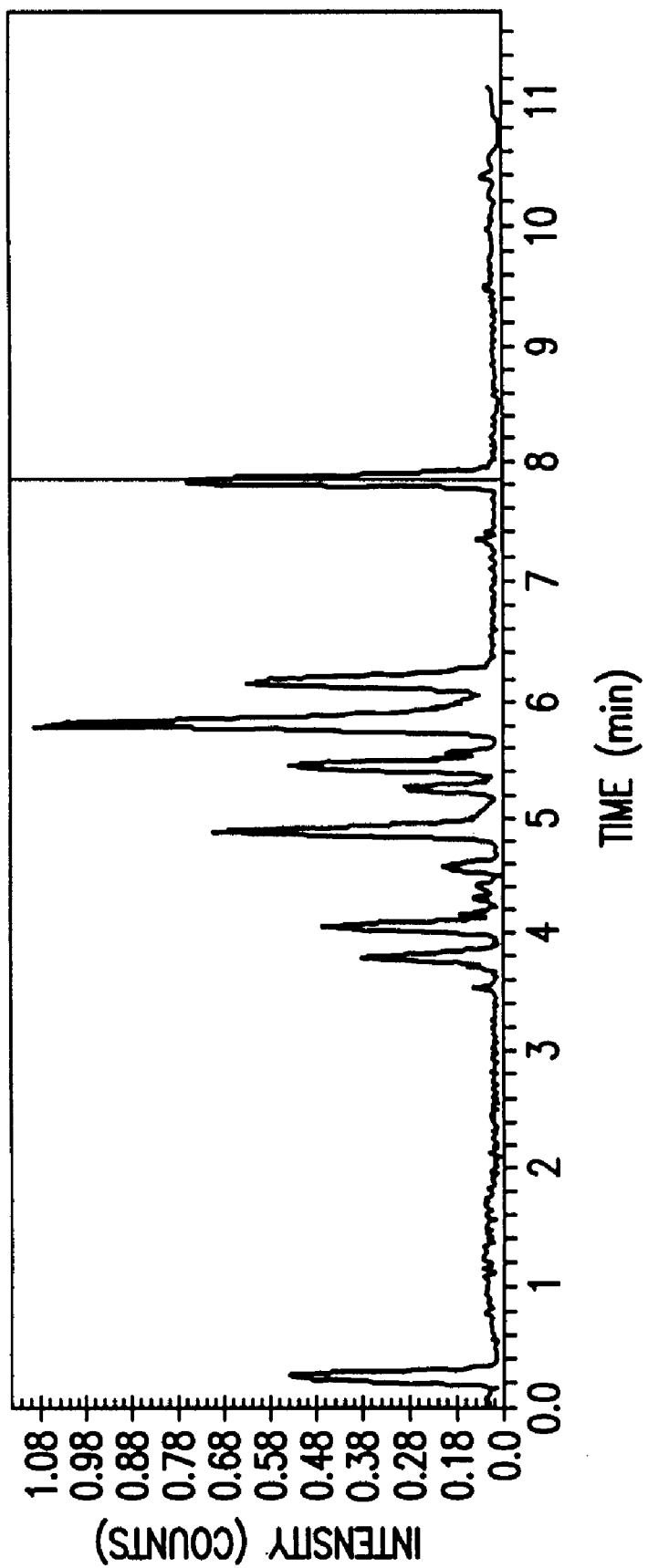

FIGS. 3–8 show an example. FIGS. 3 and 4 plot intensity (number of counts) against time, and are essentially two-dimensional representations of three-dimensional sets of data. The horizontal axis indicates the time at which a given normal or MS/MS mode spectrum was obtained. There is thus a separate spectrum for each point in time. The vertical axis represents the total summed signal (the sum of the counts) present in a given MS spectrum at each given time. Collectively, this plot is called a Total Ion Chromatogram. These data contain both normal and MS/MS mode spectra; for the sake of simplicity, only the normal mode MS spectra were used to represent the chromatograms. FIG. 3 pertains to measurements taken on a known sample, and FIG. 4 represents measurements taken on an unknown sample.

In FIG. 3, the vertical band, centered at the time of about 7.8 minutes, represents a user-defined range of times for which spectra will be taken for comparison with the unknown sample. In FIG. 4, the thin vertical bar, also located at the time of about 7.8 minutes, represents the time at which an unknown spectrum is taken. The unknown spectrum, at the time indicated by the vertical line, is to be compared with various spectra of the known sample, taken at various times within the user-defined range.

Figure 5:
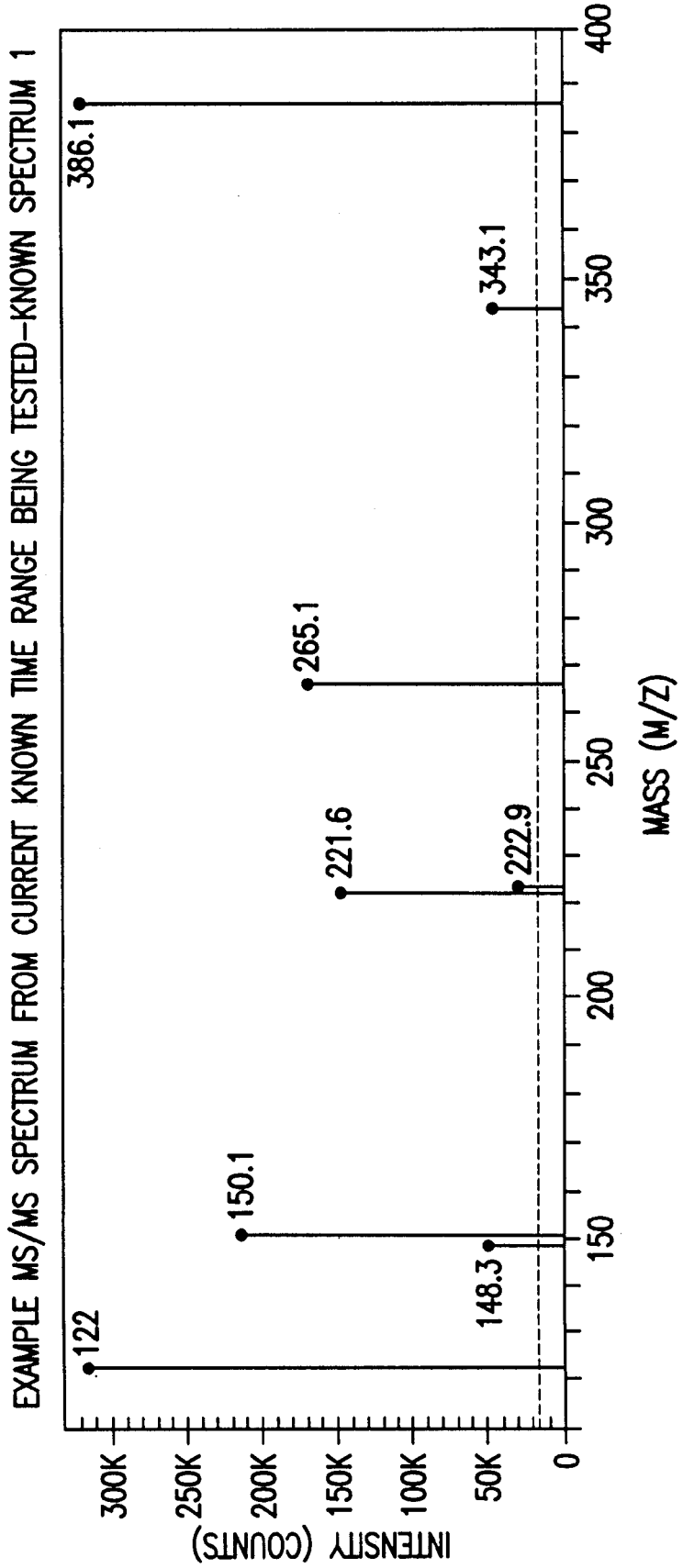
FIGS. 5–7 provide graphs representing mass spectra taken at three specific times within the range indicated in FIG. 3.
Figure 6:
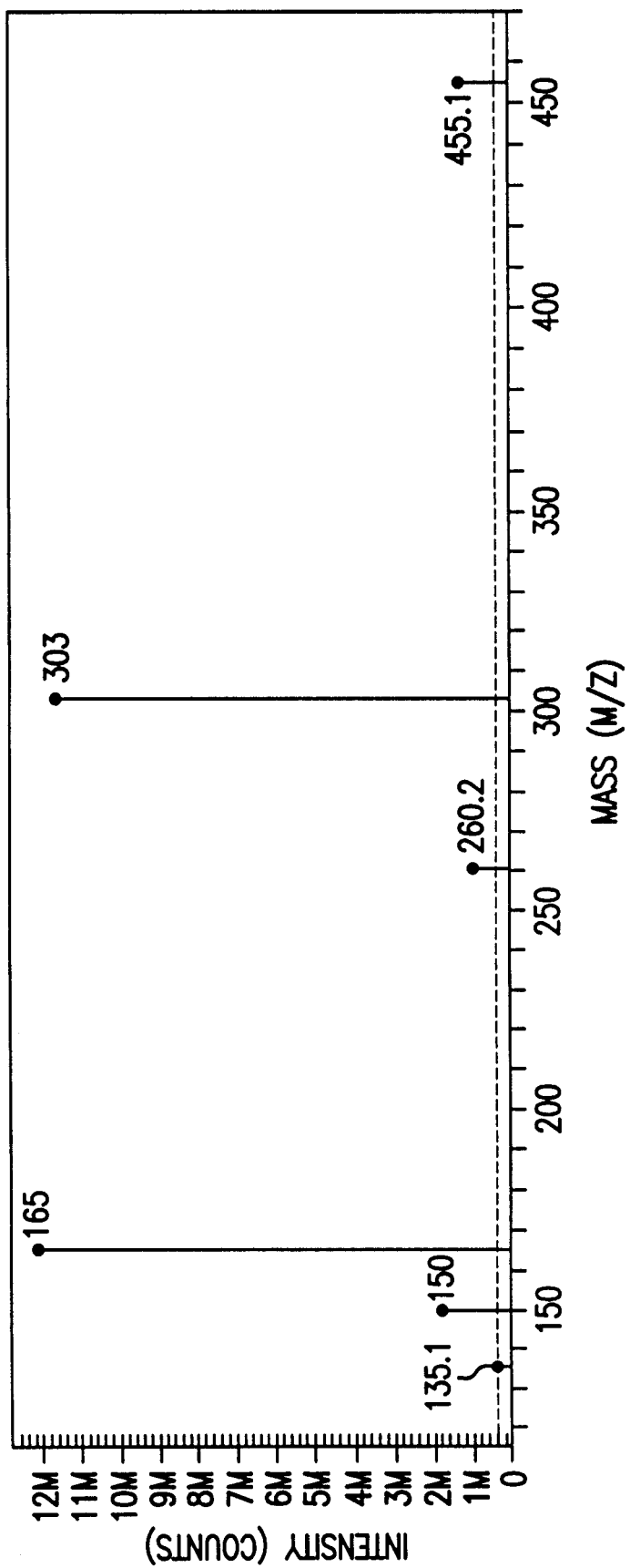
Figure 7:
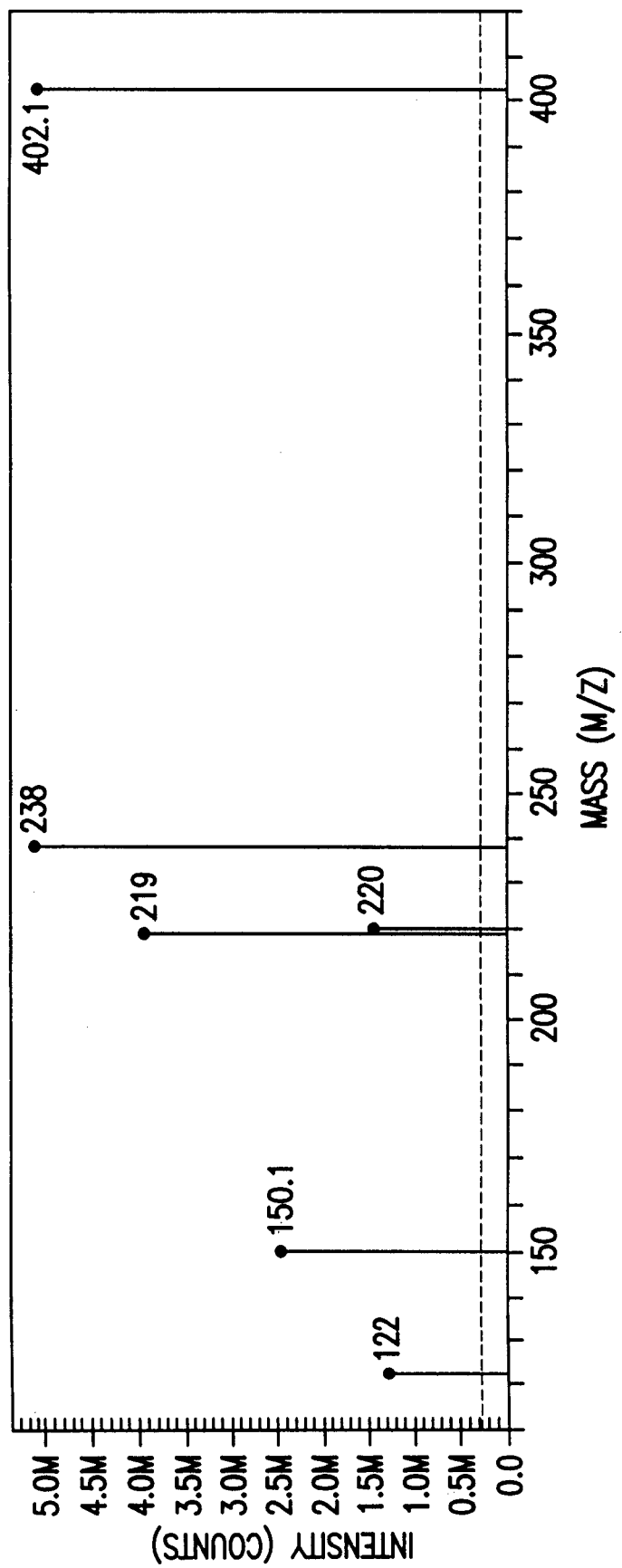
Figure 8:
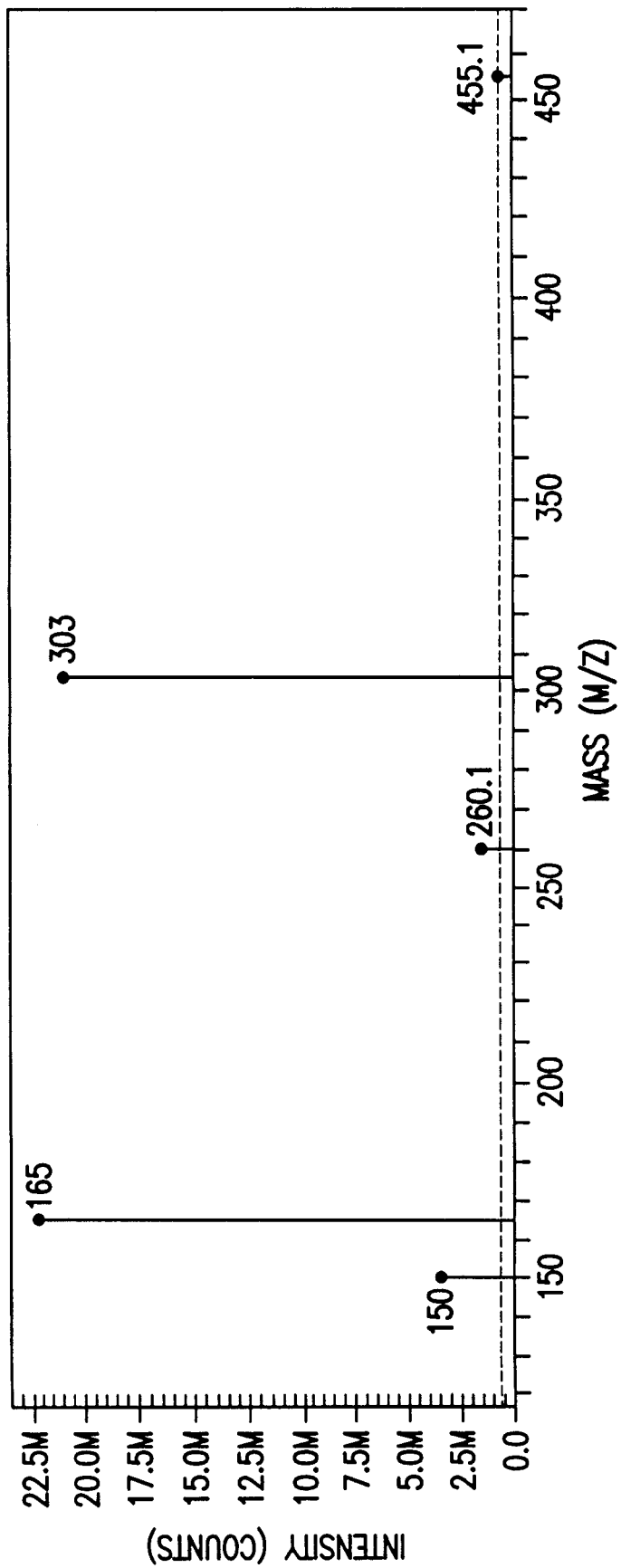
FIG. 8 provides a graph representing a mass spectrum of an unknown sample, taken at the time indicated by the vertical line in FIG. 4.

FIGS. 5–7 represent three known spectra, all taken within the user-defined range of time represented in FIG. 3. FIG. 8 represents the unknown spectrum, taken at the time represented by the vertical line in FIG. 4. In this simplified example, the spectra of FIGS. 5–7 are to be compared with that of FIG. 8.

One then correlates each known spectrum, in the chosen time interval, as represented by FIGS. 5–7, with the unknown spectrum corresponding to the selected point in time (FIG. 8). One also calculates the total signal (the sum of all counts in the graph) for each spectrum, and one also calculates the ratio of the total signal for the unknown spectrum, to the total signal for each of the known spectra. This ratio is called the total signal ratio.

The logic for determining when a candidate unknown spectrum being tested is considered unique, and worthy of further consideration, is as follows. One selects a candidate unknown spectrum for further consideration if any of the following criteria are satisfied:

a) all of the correlations between the candidate unknown spectrum and the spectra in the known range are below a user-defined threshold; or b) any of the correlations between the candidate unknown spectrum and the spectra in the known range are above a user-defined threshold, and the corresponding signal ratio is above a user-defined threshold; or c) there are no MS/MS spectra in the tested time window having the same parent mass (precursor ion) as in the unknown MS/MS spectrum.

Conversely, the candidate unknown spectrum being tested is considered a background component, and not selected for further analysis by the present invention, if the following criteria are satisfied:

a) the comparison of the candidate unknown spectrum with known spectra in the selected time interval does not result in any combination of a high correlation and high signal ratio; and b) there is at least one occurrence of both a high correlation value and a low signal ratio in the set of tested spectra.

For example, a given spectrum is therefore considered "background", and not worthy of further analysis, if it has a high correlation with one of the known spectra, and a low signal ratio, meaning that each sample contains the same component at that given time, and that component is not significantly more abundant in the unknown sample. On the other hand, the spectrum is of interest if it has a high correlation with one of the known spectra, and a high signal ratio, because the high signal ratio indicates that the unknown sample contains significantly greater amounts of the common component at that time, and therefore may be of interest. If all of the correlations between the unknown spectrum and the known spectra are low, the candidate unknown spectrum is retained for further analysis, again because it is different from all of the known spectra.

In the example shown, the hypothetical correlations and signal ratios are as shown in the following Table 3:

TABLE 3

| Known Spectrum | Correlation | User-Defined Correlation Threshold | Signal Ratio | User-Defined Signal Ratio Threshold |
|---|---|---|---|---|
| 1 | 0.03 | 0.8 | 75 | 4.0 |
| 2 | 0.98 | 0.8 | 1.8 | 4.0 |
| 3 | 0.02 | 0.8 | 4.5 | 4.0 |

In the above example, the candidate unknown spectrum is considered a background component, and would not be selected for further analysis by the present invention. Spectrum 2 in the known spectrum range has a correlation value above the user-defined threshold, and a signal ratio below the user-defined threshold. The latter indicates that the components in the candidate unknown spectrum are similar to what is in the known spectrum, and is therefore not sufficiently distinct to warrant further scrutiny. Spectra 1 and 3 have low correlation values and high signal ratios. Thus, according to the logic set forth above, the candidate unknown spectrum would be rejected. Note that, in this example, it has been assumed that the unknown spectrum had been subjected to the initial test given above, i.e. there were some cases in which the known MS/MS spectra included a parent mass which was the same as a parent mass in the unknown spectrum.

Although the above example was given with respect to liquid chromatography, the methodology described applies to any situation in which a series of mass spectra is obtained over a period of time.

Figure 9:
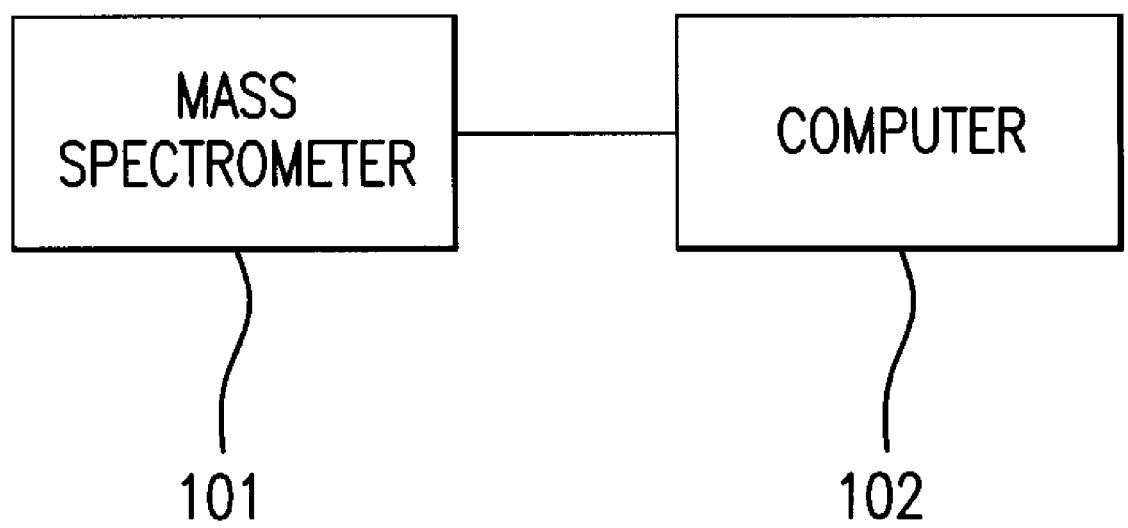
FIG. 9 provides a block diagram of the system of the present invention.

FIG. 9 shows a block diagram of the system of the present invention. Mass spectrometer 101 is connected to programmed computer 102. The computer 102 comprises the means for deriving the set of perturbed spectra, the means for comparing the spectra with the spectrum of a reference substance, and the means for choosing a best member of the set of spectra. The computer 102 also comprises means for deriving information on the molecular structure of the unknown substance, and for selecting spectra from a time series of spectra.

The invention is not limited by the specific technique of correlation. Any method which compares two spectra, i.e. two graphs or sets of ordered pairs, and which provides a scalar number representing the "relatedness" of the two spectra, can be used in the present invention. Thus, for example, instead of using cross-correlation, one could perform a least-squares analysis, or a Fourier analysis, or some other method of curve-fitting, or some other equivalent form of analysis, to make the comparison.

In the sample mass spectra shown in the figures, there is a horizontal line, above the horizontal axis, which represents a user-defined threshold. Signals below this threshold are normally ignored as they are presumed to be artifacts, and not of interest. While the use of such a threshold is preferred, the invention can be practiced without it. Moreover, the position of the threshold, if used, can be varied.

All of the above alternatives should be considered within the spirit and scope of the following claims.

What is claimed is:

1. A method of analyzing data from a mass spectrometer, comprising:
  a) generating a first mass spectrum corresponding to a known sample and a second mass spectrum corresponding to an unknown sample,
  b) applying a plurality of perturbations to said second spectrum so as to derive a plurality of perturbed spectra,
  c) comparing each of said plurality of perturbed spectra to said first mass spectrum, and
  d) choosing one of said perturbed spectra according to its correlation with said first mass spectrum,
  wherein the generating step includes generating a plurality of first and second mass spectra during a period of time, and wherein a second mass spectrum used in step (b) is selected by comparing candidate second mass spectra with a plurality of first mass spectra, and selecting a candidate second mass spectrum which contains components which are not in common with components in said first mass spectra.

2. A method of analyzing data from a mass spectrometer, comprising:
  a) generating a first mass spectrum corresponding to a known sample and a second mass spectrum corresponding to an unknown sample, wherein the first mass spectrum comprises a graph having a horizontal axis representing masses of components in the known sample, and a vertical axis representing intensity of each component, wherein the second mass spectrum comprises a graph having a horizontal axis representing masses of components in the unknown sample, and a vertical axis representing intensity of each component,
  b) applying a plurality of perturbations to said second spectrum so as to derive a plurality of perturbed spectra, wherein each perturbation comprises a shift, along the horizontal axis, of a position of one of said components,
  c) comparing each of said plurality of perturbed spectra to said first mass spectrum, and
  d) choosing one of said perturbed spectra according to its correlation with said first mass spectrum,
  wherein the generating step includes generating a plurality of first and second mass spectra during a period of time, and wherein a second mass spectrum used in step (b) is selected by comparing candidate second mass spectra with a plurality of first mass spectra, and selecting a candidate second mass spectrum which contains components which are not in common with components in said first mass spectra.

* * * * *